United States Patent [19]
Illian et al.

[11] Patent Number: 5,849,216
[45] Date of Patent: Dec. 15, 1998

[54] COMPOUNDS FOR USE IN LIQUID-CRYSTAL MIXTURES

[75] Inventors: Gerd Illian, Tokyo, Japan; Anke Kaltbeitzel, Rüsselsheim, Germany; Rainer Wingen, Hattersheim am Main, Germany; Hubert Schlosser, Glashütten/Taunus, Germany

[73] Assignee: Hoechst Aktiengesellschaft, Frankfurt, Germany

[21] Appl. No.: 454,995

[22] Filed: May 31, 1995

Related U.S. Application Data

[63] Continuation of Ser. No. 320,979, Oct. 11, 1994, abandoned, which is a continuation of Ser. No. 988,899, Nov. 5, 1992, abandoned.

[30] Foreign Application Priority Data

Nov. 7, 1991 [DE] Germany .......................... 41 36 627.1

[51] Int. Cl.$^6$ ............................ C09K 19/34; C09K 19/30
[52] U.S. Cl. ................................ 252/299.61; 252/299.63; 252/299.68; 544/296; 544/238; 544/310; 544/333; 544/334; 544/335; 546/255; 546/256; 546/257; 546/258; 549/414; 549/415; 548/128; 548/129; 548/125
[58] Field of Search ...................... 548/136; 252/299.61, 252/299.63, 299.68

[56] References Cited

U.S. PATENT DOCUMENTS

| | | | |
|---|---|---|---|
| 4,704,227 | 11/1987 | Krause et al. ........................... | 514/183 |
| 4,874,544 | 10/1989 | Yong et al. ......................... | 252/299.61 |
| 4,952,699 | 8/1990 | Yong et al. ......................... | 548/136 |
| 5,034,151 | 7/1991 | Shinjo et al. ........................... | 514/183 |
| 5,076,961 | 12/1991 | Nakamura et al. ..................... | 514/183 |
| 5,098,600 | 3/1992 | Nakamura et al. ................. | 252/299.61 |
| 5,232,624 | 8/1993 | Reiffenrath et al. ............... | 252/299.61 |

FOREIGN PATENT DOCUMENTS

| | | |
|---|---|---|
| 2021486 | 1/1991 | Canada . |
| 0 022 882 | 1/1981 | European Pat. Off. . |
| 0 087 679 | 9/1983 | European Pat. Off. . |
| 0 090 671 | 10/1983 | European Pat. Off. . |
| 0 097 033 | 12/1983 | European Pat. Off. . |
| 0 154 840 | 9/1985 | European Pat. Off. . |
| 0 196 070 | 10/1986 | European Pat. Off. . |
| 0 336 619 | 10/1989 | European Pat. Off. . |
| 0 347 811 | 12/1989 | European Pat. Off. . |
| 0 354 655 | 2/1990 | European Pat. Off. . |
| 0 381 149 | 8/1990 | European Pat. Off. . |
| 0 400 741 | 12/1990 | European Pat. Off. . |
| 0 409 368 | 1/1991 | European Pat. Off. . |
| 0 409 369 | 1/1991 | European Pat. Off. . |
| 117 014 | 12/1975 | Germany . |
| 29 33 544 | 3/1981 | Germany . |
| WO 88/02390 | 4/1988 | WIPO . |

OTHER PUBLICATIONS

J. P. Schroeder and D. W. Bristol, Journal of Orgainc Chemistry, vol. 38, No. 18, pp. 3160–3164, 1973.
J. W. Brown, et al., Molecular Crystals and Liquid Crystals, vol. 173, pp. 121–140, 1989.
D. J. Bryon, et al., Molecular Crystals and Liquid Crystals, vol. 62, Nos. 1 and 2, pp. 103–114, 1980.
H. Zaschke, et al., Journal Für Praktische Chemie, vol. 315, No. 6, pp. 1113–1120, 1973 (plus translation from Chemical Abstracts).
K. Dölling, et al., Journal Für Praktische Chemie, vol. 321, No. 4, pp. 643–654, 1979 (plus translation from Chemical Abstracts).
D. Demus, H. Zaschke, Flüssigkristalle in Tabellen, Bd. 2, 1. Auflage, S. 360 VEB Deutscher Verlag für Grundstoffindustrie Leipzig, 1984.
Chemical Abstracts CA101(12) 101211d On–Line Print–out and Registry Citation for 1456–67–3.
Liquid Crystals Applications and Uses, B. Bahadur, Ed., World Scientific Publishing Co. (New Jersey), pp. 102 and 103 (1990).
Diele et al., Chemical Abstracts 112:46139, 1989. (See Online printout).
Dimitrova, Chemical Abstracts 94:174993, 1980. (See Online printout).

*Primary Examiner*—Matthew V. Grumbling
*Attorney, Agent, or Firm*—Frommer Lawrence & Haug LLP

[57] ABSTRACT

Compounds of the formula (I)

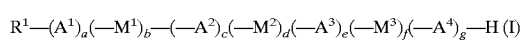

in which the symbols and indices have the following meanings:

$R^1$ is B or a straight-chain or branched alkyl radical having 1 to 22 carbon atoms (with or without an asymmetrical carbon atom) in which, in addition, it is possible for one or two non-adjacent —$CH_2$— groups to be replaced by —O—, —S—, —CO—, —CO—O—, —O—CO—, —CO—S—, —S—CO—, —O—CO—O—, —CH=CH—, —C≡C—, Δ or —Si$(CH_3)_2$—, and in which, in addition, one or more hydrogen atoms of the alkyl radical may be substituted by F, Cl, Br or CN, or is a chiral group, for example an epoxide, a dioxolane or a cyclic lactone, —$(A^1)_a$(—$M^1)_b$—(—$A^2)_c$(—$M^2)_d$(—$A^3)_e$(—$M^3)_f$(—$A^4)_g$— is a system comprising 1 to 4 rings (cyclohexane, aromatic or heterocyclic), it being possible for the system to be linked in different ways.

The compounds according to the invention increase the response speed of liquid-crystal mixtures.

7 Claims, No Drawings

COMPOUNDS FOR USE IN LIQUID-CRYSTAL MIXTURES

This application is a continuation of application Ser. No. 08/320,979, filed Oct. 11, 1994, abandoned, which is a continuation of Ser. No. 07/988,899 filed on Nov. 5, 1992, now abandoned.

In particular in the last decade, liquid crystals have been introduced into various technical areas where electro-optical and display device properties are required (for example in watch, calculator and typewriter displays). These display devices are based on the dielectric alignment effects in the nematic, cholesteric and/or smectic phases of the liquid-crystalline compounds, where, caused by the dielectric anisotropy, the molecular long axes of the compounds adopt a preferred alignment in an applied electric field. The conventional response times in these display devices are too long for many other potential areas of application of liquid crystals. This disadvantage is particularly noticeable if a large number of pixels have to be addressed. The production costs of equipment containing relatively large screen areas are then generally too high.

In addition to nematic and cholesteric liquid crystals, optically active smectic liquid-crystal phases have also been increasing in importance for a few years.

Clark and Lagerwall have been-able to show that the use of ferroelectric liquid-crystal systems in very thin cells give electro-optical switch or display elements which have response times faster by a factor of up to 1000 compared with conventional TN ("twisted nematic") cells (cf., for example, Lagerwall et al., "Ferroelectric Liquid Crystals for Displays", SID Symposium, October Meeting 1985, San Diego, Calif., U.S.A.). Due to these and other favorable properties, for example the possibility for bistable switching and the contrast which is virtually independent of the viewing angle, FLCs are fundamentally very suitable for the abovementioned areas of application, for example via matrix addressing. Due to their high contrast and speed, ferroelectric liquid crystals are also particularly suitable in the area of spatial light modulators (cf., for example, U. Efron in "Spatial Light Modulators and Applications", SPIE, Vol. 1150, p. 46 ff). However, ferroelectric liquid-crystal mixtures are generally not fast enough to drive, for example, high-resolution, fast display elements. It is therefore desirable to find components which increase the response speed of liquid-crystalline mixtures. The invention therefore relates to components which shorten the response time of liquid-crystal mixtures.

Liquid crystals containing only one side chain have been paid little attention. Examples are found in: D. Demus, H. Zaschke, "Flüissigkristalle in Tabellen" [Liquid Crystals in Tables], Vol. 2, 1st Edn., VEB Deutscher Verlag für Grundstoffindustrie, Leipzig, 1984, p. 360. Since the phase properties of these substances appear unfavorable compared with mesogenic compounds containing two side chains, they have hitherto not been employed in mixtures.

Surprisingly, it has now been found that compounds of the formula I containing only one side chain considerably increase the response speed of liquid-crystal mixtures.

The invention therefore relates to compounds of the formula I:

$$R^1-(A^1)_a(-M^1)_b-(-A^2)_c(-M^2)_d(-A^3)_e(-M^3)_f(-A^4)_g-H \quad (I)$$

in which the symbols and indices have the following meanings:

$R^1$ is H or a straight-chain or branched alkyl radical having 1 to 22 carbon atoms (with or without an asymmetrical carbon atom) in which, in addition, it is possible for one or two non-adjacent —$CH_2$— groups to be replaced by —O—, —S—, —CO—, —CO—O—, —O—CO—, —CO—S—, —S—CO—, —O—CO—O—, —CH=CH—, —C≡C—, $\Delta$ or —Si($CH_3$)$_2$—, and in which, in addition, one or more hydrogen atoms of the alkyl radical may be substituted by F, Cl, Br or CN, or is one of the chiral groups below:

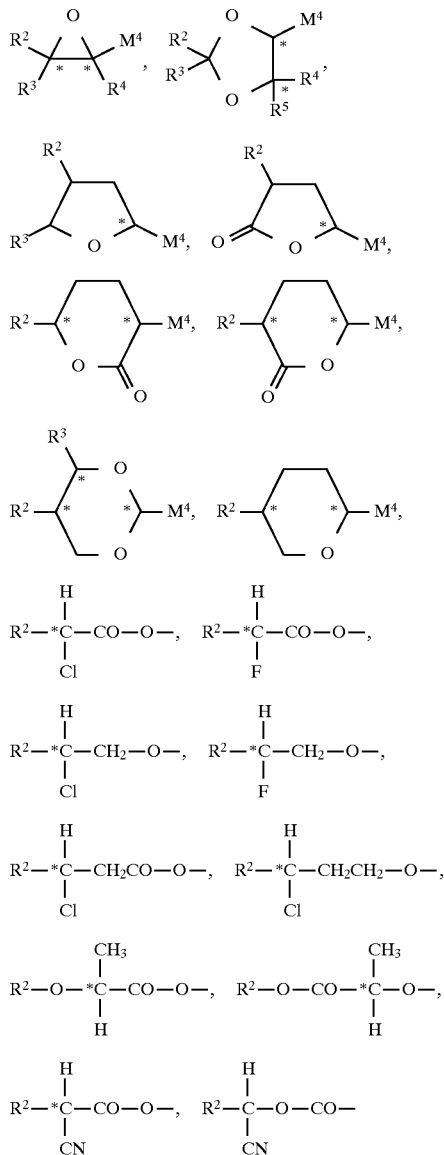

$R^2$, $R^3$, $R^4$ and $R^5$, independently of one another, are H or a straight-chain or branched alkyl radical having 1 to 22 carbon atoms in which, in addition, it is possible for one or two non-adjacent —$CH_2$—groups to be replaced by —O—, —S—, —CO—, —CO—O—, —O—CO—, —CO—S—, —S—CO—, —O—CO—O—, —CH=CH—, —C≡C—, $\Delta$ or —Si($CH_3$)$_2$—, or $R^2$ and $R^3$ together may alternatively be —($CH_2$)$_4$— or —($CH_2$)$_5$— if they are bonded as substituents to a dioxolane system;

$A^1$, $A^2$, $A^3$ and $A^4$ are identical or different and are 1,4-phenylene, in which one or two hydrogen atoms may be replaced by F, Cl and/or CN, pyrazine-2,5-diyl, pyridazine-3,6-diyl, pyridine-2,5-diyl, pyrimidine-2,5-diyl, in which one or two hydrogen atoms may be replaced by F, trans-1,4-cyclohexylene, in which one or two hydrogen atoms may be replaced by —CN and/or —CH$_3$, 1,3,4-thiadiazole-2,5-diyl, 1,3-dioxane-2,5-diyl, 1,3-dithiane-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2,5-diyl, naphthalene-2,6-diyl, bicyclo[2.2.2]octane-1,4-diyl, 1,3-dioxaborinane-2,5-diyl or trans-decalin-2,6-diyl;

$M^1$, $M^2$ and $M^3$ are identical or different and are —O—, —S—, —CO—, —CO—O—, —O—CO—, —CO—S—, —S—CO—, —O—CO—O—, —CH$_2$—O—, —O—CH$_2$—, —CH$_2$CH$_2$—, —CH=CH— or —C≡C—;

$M^4$ is —CH$_2$—O—, —O—CH$_2$—, —CO—O—, —O—CO— or a single bond;

a, b, c, d, e, f and g are zero or one, with the proviso that the sum a+c+e+g is 1, 2, 3 or 4,

* is a chiral center;

apart from the compound in which the $(A^1)_a(-M^1)_b(-A^2)_c(-M^2)_d(-A^3)_e(M^3)_f(-A^4)_g$—H group is

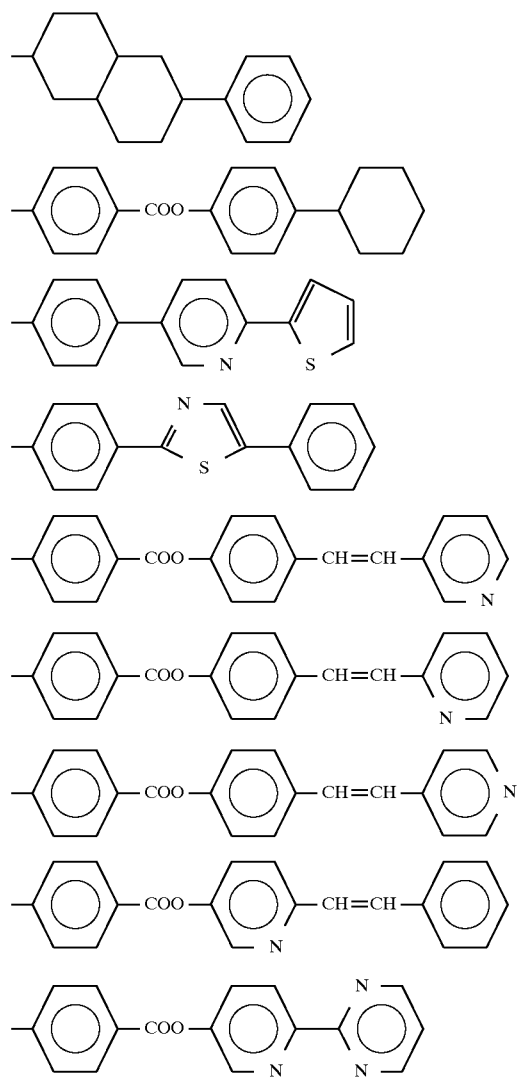

-continued

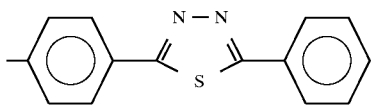

The invention furthermore relates to the use of all the compounds of the formula I, individually or in mixtures, in liquid-crystal mixtures.

Preference is given to compounds of the formula (I) in which the symbols and indices have the following meanings, with retention of the above-described exceptions:

$R^1$ is H or a straight-chain or branched alkyl radical having 1 to 22 carbon atoms (with or without an asymmetrical carbon atom) in which, in addition, one or two non-adjacent —CH$_2$— groups may be replaced by —O—, —S—, —CO—, —CO—O—, —O—CO—, —O—CO—O—, —CH=CH—, —C≡C—, Δ or —Si(CH$_3$)$_2$—, or is one of the chiral groups below:

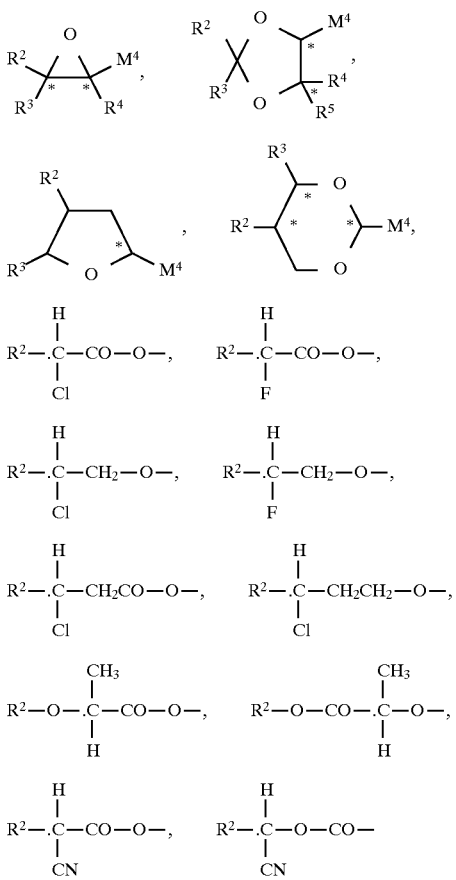

$R^2$, $R^3$, $R^4$ and $R^5$, independently of one another, are H or a straight-chain or branched alkyl radical having 1 to 22 carbon atoms in which, in addition, one or two non-adjacent —CH$_2$— groups may be replaced by —O—, —S—, —CO—, —CO—O—, —O—CO—, —CO—S—, —S—CO—, —O—CO—O—, —CH=CH—, —C≡C—, Δ or —Si(CH$_3$)$_2$—, or $R^2$ and $R^3$ together may alternatively be —(CH$_2$)$_4$— or —(CH$_2$)$_5$— if they are bonded as substituents to a dioxolane system;

$A^1$, $A^2$, $A^3$ and $A^4$ are identical or different and are 1,4-phenylene, pyrazine-2,5-diyl, pyridazine-3,6-diyl, pyridine-2,5-diyl, pyrimidine-2,5-diyl, trans-1,4-cyclohexylene, 1,3,4-thidiazole-2,5-diyl, 1,3-dioxane-2,5-diyl, naphthalene-2,6-diyl or bicyclo[2.2.2]octane-1,4-diyl;

$M^1$, $M^2$ and $M^3$ are identical or different and are —O—, —CO—, —CO—O—, —O—CO—, —CH$_2$—O—, —O—CH$_2$—, —CH$_2$CH$_2$—, —CH=CH— or —C≡C—;

$M^4$ is —CH$_2$—O—, —O—CH$_2$—, —CO—O—, —O—CO— or a single bond.

Particular preference is given to compounds of the formula (I) in which the symbols and indices have the following meanings, with retention of said exceptions:

$R^1$ is H or a straight-chain or branched alkyl radical having 1 to 22 carbon atoms (with or without an asymmetrical carbon atom) in which, in addition, one or two non-adjacent —CH$_2$— groups may be replaced by —O—, —CO—, —CO—O—, —O—CO—, —CH=CH—, —C≡C—, Δ or —Si(CH$_3$)$_2$—, or is one of the chiral groups below:

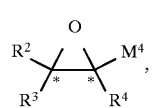 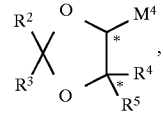

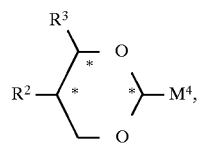

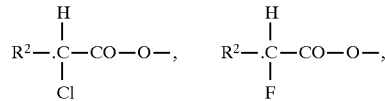

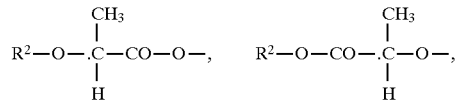

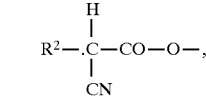

$R^2$, $R^3$, $R^4$ and $R^5$, independently of one another, are H or a straight-chain or branched alkyl radical having 1 to 22 carbon atoms in which, in addition, one or two non-adjacent —CH$_2$— groups may be replaced by —O—, —S—, —CO—, —CO—O—, —O—CO—, —CO—S—, —S—CO—, —O—CO—O—, —CH=CH—, —C≡C—, Δ or —Si(CH$_3$)$_2$—, or $R^2$ and $R^3$ together may alternatively be —(CH$_2$)$_4$— or —(CH$_2$)$_5$— if they are bonded as substituents to a dioxolane system;

$A^1$, $A^2$, $A^3$ and $A^4$ are identical or different and are 1,4-phenylene, pyrazine-2,5-diyl, pyridine-2,5-diyl, pyrimidine-2,5-diyl, trans-1,4-cyclohexylene, 1,3,4-thiadiazole-2,5-diyl, naphthalene-2,6-diyl or 1,3-dioxane-2,5-diyl;

$M^1$, $M^2$ and $M^3$ are identical or different and are —O—, —CO—O—, —O—CO—, —CH$_2$—O—, —O—CH$_2$—, —CH$_2$—CH$_2$—, —CH=CH— or C=C—;

$M^4$ is —CH$_2$—O—, —O—CH$_2$—, —CO—O—, —O—CO— or a single bond.

Very particular preference is given to compounds of the formula (I) in which, with retention of the above-mentioned exception, $R^1$ is H or an alkyl radical having 1 to 22 carbon atoms, in which one —CH$_2$— group may be replaced by —O—, Δ, —CH=CH— or —Si(CH$_3$)$_2$—, or is the chiral group

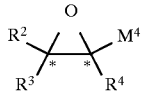

and the $(—A^1)_a(—M^1)_b—(—A^2)_c(—M^2)_d(—A^3)_e(—M^3)_f(—A^4)_g$ group has the following meaning:

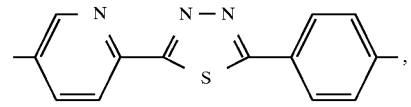

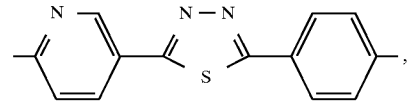

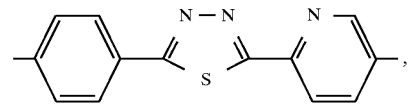

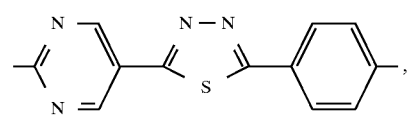

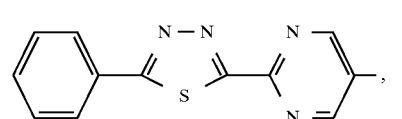

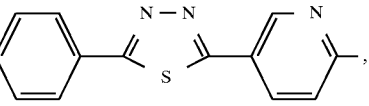

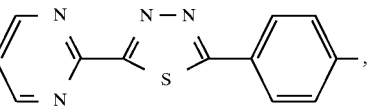

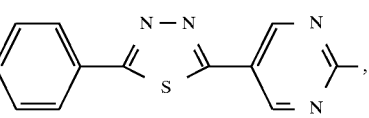

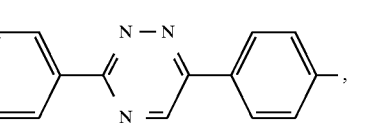

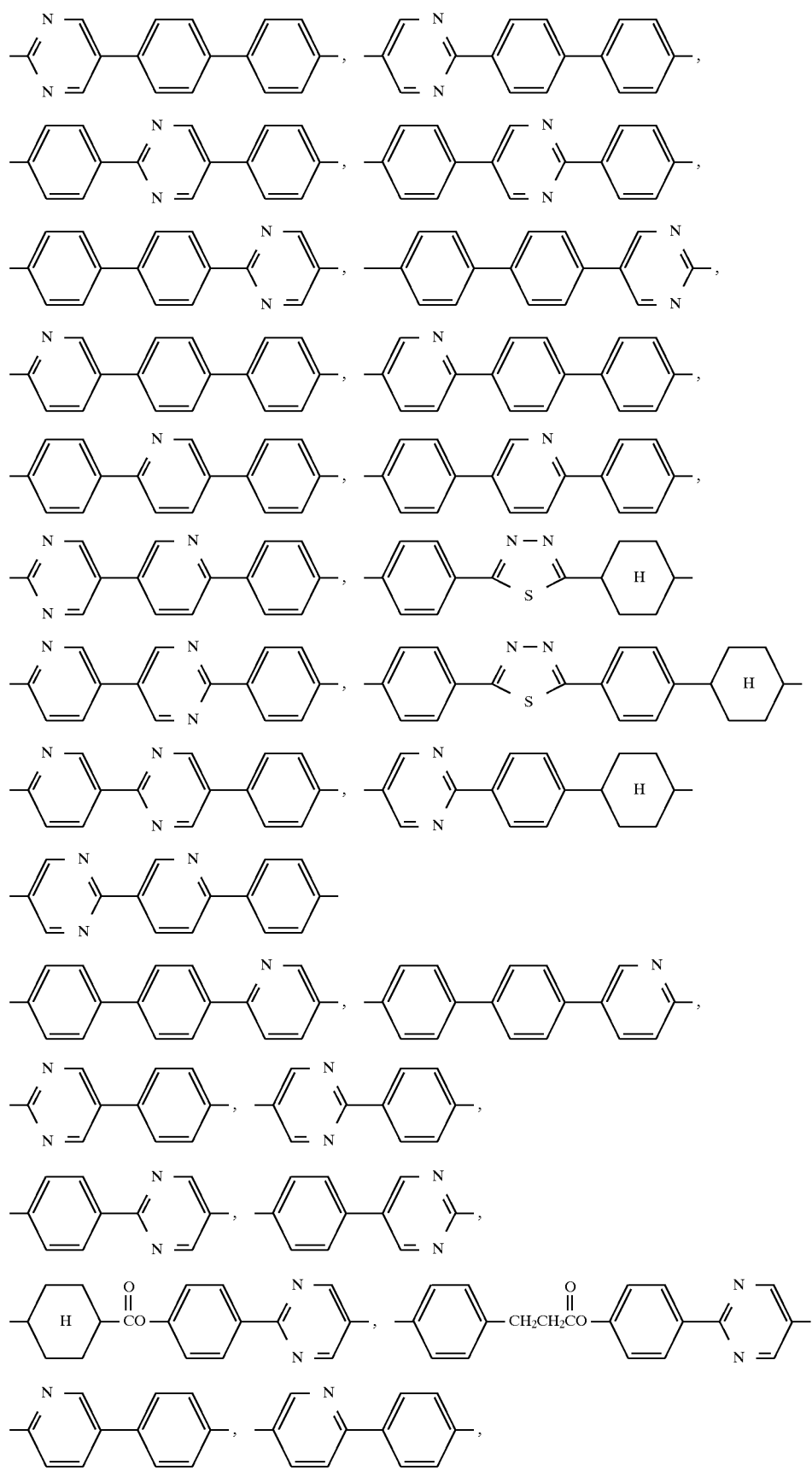

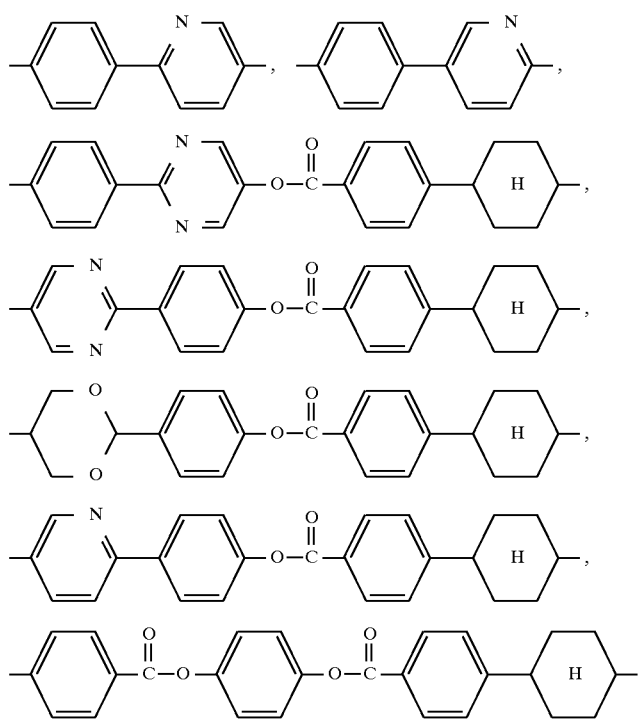

The compounds according to the invention can be prepared by methods known per se from the literature (see, for example, Houben-Weyl, Methoden der Organischen Chemie [Methods of Organic Chemistry], Georg-Thieme-Verlag, Stuttgart; K. Dimitrowa, J. Hauschild, H. Zaschke and H. Schubert, Journal für praktische Chemie, Vol. 322 (1980), page 933; H. Zaschke and H. Schubert, Journal für praktische Chemie, Vol. 315 (1973), page 315).

The compounds of the formula I according to the invention are suitable as components for liquid-crystal mixtures, in particular ferroelectric liquid-crystal mixtures. The LC mixtures may contain from 0.01 to 60% by weight, preferably from 0.1 to 40% by weight, particularly preferably from 0.1 to 20% by weight, of the compounds according to the invention. The other constituents are preferably selected from known compounds having nematic, cholesteric and/or smectic phases; these include, for example, Schiff's bases, biphenyls, terphenyls, phenyl-cyclohexanes, cyclohexylbiphenyls, N-, S- or O-containing heterocyclic compounds, for example pyrimidines, cinnamic acid esters, cholesterol esters or various bridged, polycyclic esters of p-alkylbenzoic acids which have terminal polar groups.

Surprisingly, it has now been found that the addition of compounds of the formula I can considerably increase the response speed of these liquid-crystal mixtures.

These mixtures can in turn be used in electro-optical or fully optical elements, for example display elements, switching elements, light modulators, elements for image processing, signal processing or generally in the area of non-linear optics.

The invention is described in greater detail by means of the examples below: for the ferroelectric liquid-crystal mixtures, the values for spontaneous polarization $P_s$[nC/cm$^2$] and the electrical response time $\tau$[$\mu$s] were measured at a temperature of 25° C.

The $P_s$ values were measured by the method of H. Diamant et al. (Rev. Sci. Instr., 28, 30, 1957), using measurement cells having an electrode separation of 10 $\mu$m and no alignment layer.

The phase transition temperatures were determined with the aid of a polarizing microscope from the changes in texture on heating. By contrast, the melting point was determined using a DSC instrument. The phase transition temperatures between the phases

| nematic | (N or N*) |
| smectic-C | ($S_c$ or $S_c$*) |
| smectic-A | ($S_A$) |
| crystalline | (X) | are given in °C., and the values are between the phase designations in the phase sequence.

EXAMPLE 1

2-(4-Decyloxyphenyl)-5-phenyl-1,3,4-thiadiazole

The synthesis was carried out analogously to the method described by K. Dimitrowa, J. Hauschild, H. Zaschke and H. Schubert in Journal fur praktische Chemie, Vol. 322 (1980), page 933.

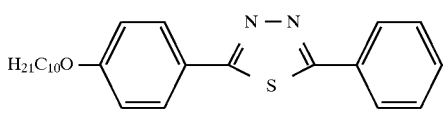

The compound has the following phase sequence:

X 99 $S_A$ 128 I

EXAMPLE 2

2-(4-Decylphenyl)-5-phenyl-1,3,4-thiadiazole

The synthesis was carried out analogously to Example 1.

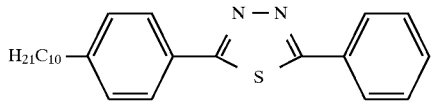

The compound has the following phase sequence:
X 70 $X_1$ 81 $S_A$ 88 I

EXAMPLE 3

2-(4-Nonylphenyl)-5-phenyl-1,3,4-thiadiazole

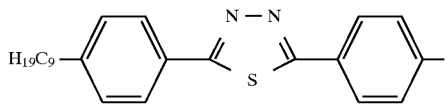

The synthesis was carried out analogously to Example 1.
The compound has the following phase sequence:
X 81 $S_A$ 87 N 87.4 I

EXAMPLE 4

2-(4-Octyloxyphenyl)-5-phenyl-1,3,4-thiadiazole

The synthesis was carried out analogously to Example 1.

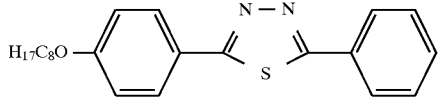

The compound has the following phase sequence:
X 103 $S_A$ 124 N 125 I

EXAMPLE 5

2-(4-Nonyloxyphenyl)-5-phenyl-1,3,4-thiadiazole

The synthesis was carried out analogously to Example 1.

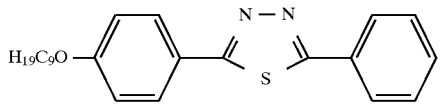

The compound has the following phase sequence:
X 97 $S_A$ 127 I

EXAMPLE 6

2-(4-Dodecylphenyl)-5-phenyl-1,3,4-thiadiazole

The synthesis was carried out analogously to Example 1.

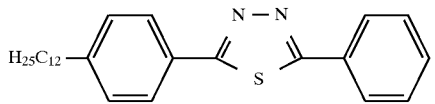

The compound has the following phase sequence:
X 67 $S_A$ 89 I

EXAMPLE 7

2-(4-Dodecyloxyphenyl)-5-phenyl-1,3,4-thiadiazole

The synthesis was carried out analogously to Example 1.

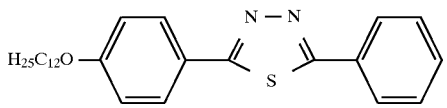

The compound has the following phase sequence:
X 84 $S_A$ 127 I

EXAMPLE 8

2-(4-Hexadecyloxyphenyl)-5-phenyl-1,3,4-thiadiazole

The synthesis was carried out analogously to Example 1.

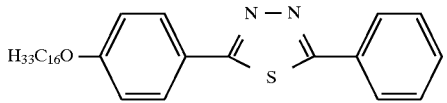

The compound has the following phase sequence:
X 75 $S_A$ 125 I

EXAMPLE 9

2-(4-Butoxyphenyl)-5-phenyl-1,3,4-thiadiazole

The synthesis was carried out analogously to Example 1.

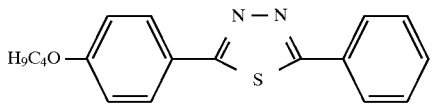

The compound has the following phase sequence:
X 97 $S_x$ 87 $S_C$ 89 $S_A$ 95 N 108 I

EXAMPLE 10

2-(4-Hexyloxyphenyl)-5-phenyl-1,3,4-thiadiazole

The synthesis was carried out analogously to Example 1.

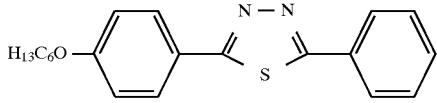

The compound has the following phase sequence:
$X_1$ 89 $X_2$ 94 $S_A$ 111 N 119 I

EXAMPLE 11

2-Phenyl-5-(4-tetradecyloxyphenyl)-1,3,4-thiadiazole

The synthesis was carried out analogously to Example 1.

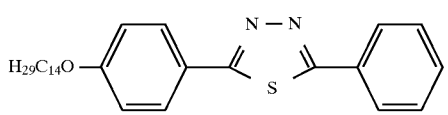

The compound has the following phase sequence:
X 90 S$_A$ 131 I

EXAMPLE 12

2-Cyclohexyl-5-(4-nonyloxyphenyl)-1,3,4-thiadiazole

The synthesis was carried out analogously to Example 1.

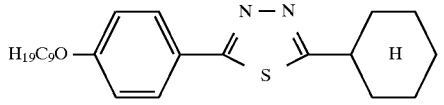

The compound has the following phase sequence:
X$_1$ 77 X$_2$ 86 S$_A$ 67 I

EXAMPLE 13

2-(4-Cyclohexylphenyl)-5-(4-nonyloxyphenyl)-1,3,4-thiadiazole

The synthesis was carried out analogously to Example 1.

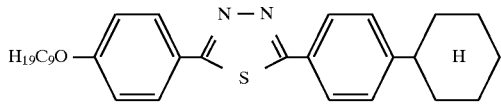

The compound has the following phase sequence:
S 126 S$_C$ 146 N 186 I

EXAMPLE 14

2-(4-Octyloxyphenyl)-5-phenylpyrimidine

The synthesis was carried out as described by H. Zaschke and H. Schubert in Journal fur praktische Chemie, Vol. 315 (1973), page 315.

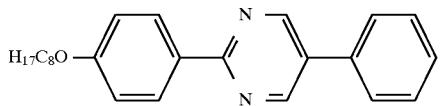

The compound has the following phase sequence:
X 100 N 113 I

EXAMPLE 15

2-(4-Dodecyloxyphenyl)-5-phenylpyrimidine

The synthesis was carried out analogously to Example 14.

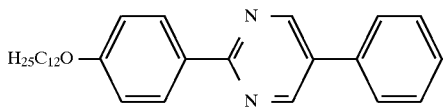

The compound has the following phase sequence:
X 103 N 109 I

EXAMPLE 16

5-(4-Dodecyloxyphenyl)-2-phenylpyrimidine

The synthesis was carried out analogously to Example 14.

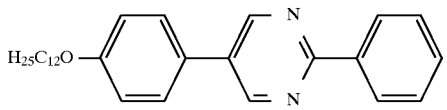

The compound has the following phase sequence:
X 93 S$_A$ 156 I

EXAMPLE 17

5-(4-Hexyloxyphenyl)-2-phenylpyrimidine

The synthesis was carried out analogously to Example 14.

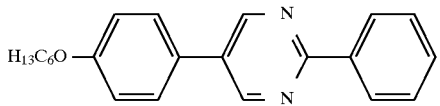

The compound has the following phase sequence:
X 92 S$_A$ 163 I

EXAMPLE 18

5-(4-Hexylphenyl)-2-phenylpyrimidine

The synthesis was carried out analogously to Example 14.

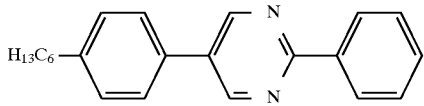

The compound has the following phase sequence:
X 97 S$_A$ 133 I

EXAMPLE 19

2-(4-Octyloxyphenyl)pyrimdin-5-yl 4-cyclohexylphenylcarboxylate 2.00 g (6.66 mmol) of 2-(4-octyloxyphenyl)-5-hydroxypyrimine, 1.36 g (6.66 mmol) of 4-cyclohexylphenylcarboxylic acid, 1.37 g (6.66 mmol) of dicyclohexylcarbodiimide and a spatula tip of N,N-dimethylaminopyridine were stirred at room temperature for 17 hours. The mixture was subsequently filtered, the filtrate was evaporated, and the residue was chromatographed on silica gel using hexane:ethyl acetate=8:2. Recrystallization from hexane gave 2.13 g of 2-(4-octyloxyphenyl)pyrimidin-5-yl 4-cyclohexylphenylcarboxylate.

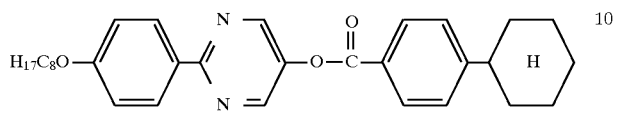

The compound has the following phase sequence:
X 108 N 206 I

EXAMPLE 20

4-(5-Octyl-1,3-dioxan-2-yl)phenyl 4-cyclohexylphenylcarboxylate

The synthesis was carried out analogously to Example 19.

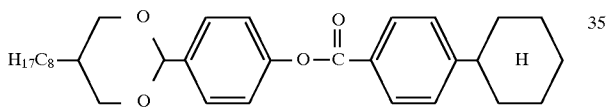

The compound has the following phase sequence:
X 106 N 169 I

EXAMPLE 21

4-(5-Octylpyridin-2-yl)phenyl 4-cyclohexylphenylcarboxylate

The synthesis was carried out analogously to Example 19.

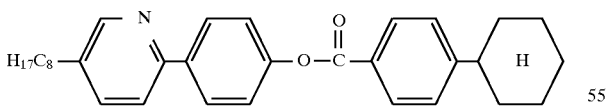

The compound has the following phase sequence:
X 133 N 182 I

EXAMPLE 22

4-(5-Octyloxypyrimidin-2-yl)phenyl 4-cyclohexylphenylcarboxylate

The synthesis was carried out analogously to Example 19.

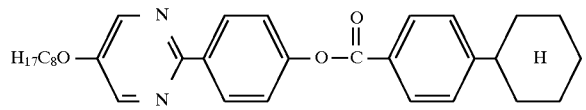

The compound has the following phase sequence:
X 144 N 200 I

EXAMPLE 23

4-(4-Octyloxyphenylcarbonyloxy)phenyl 4-cyclohexylphenylcarboxylate

The synthesis was carried out analogously to Example 19.

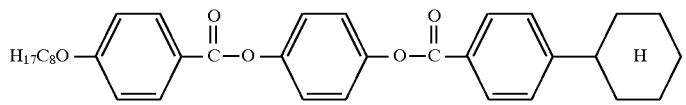

The compound has the following phase sequence:
X 146 N 212 I

EXAMPLE 24

4-(Pyrimidin-2-yl)phenyl trans-4-pentylcyclohexanecarboxylate

The synthesis was carried out analogously to Example 19.

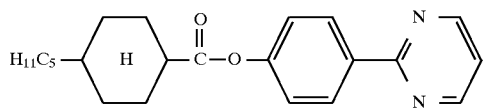

The compound has the following phase sequence:
X 117 I

EXAMPLE 25

4-(Pyrimidin-2-yl)phenyl 3-(4-ethylphenyl)propanoate

The synthesis was carried out analogously to Example 19.

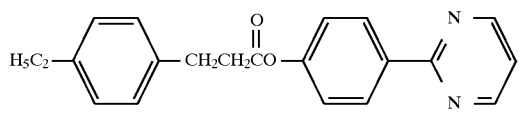

The compound has the following phase sequence:
X 113 I

EXAMPLE 26

2-(4-Octyloxyphenyl)pyrimidine 0.30 g (7.50 mmol) of 60% strength sodium hydride are added in portions to 0.86 g (5.00 mmol) of 2-(4-hydroxyphenyl)pyrimidine in 40 ml of dimethylformamide, and the mixture is stirred at room temperature for 15 minutes. 1.45 g (7.50 mmol) of 1-bromooctane are subsequently added, the mixture is stirred overnight, poured into ice water and filtered, and the residue is purified by chromatography (silica gel/dichloromethane) and by recrystallization from acetonitrile, giving 0.93 g of 2-(4-octyloxyphenyl)pyrimidine.

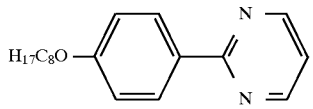

The compound has the phase sequence:

X 51 I

EXAMPLE 27

5-(2-Octyloxypyrimidin-5-yl)-2-phenylpyridine

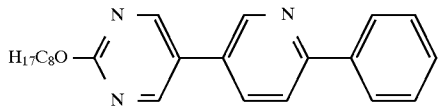

The synthesis was carried out analogously to the procedures in Tetrahedron Letters 28 (1987) 5093 and Mol. Cryst. Liq. Cryst. 204 (1991) 91 or Mol. Cryst. Liq. Cryst. 206 (1991) 187 or J. Chem. Soc. Perkin. Trans. II 1989, 2041, from 2-octyloxy-5-bromopyrimidine and 2-phenylpyridine-5-boronic acid.

The compound has the following phase sequence:

X 133 SA 153 I

EXAMPLE 28

5-[2-(9-Decenyloxy)pyrid-5-yl]-2-phenylpyrimidine

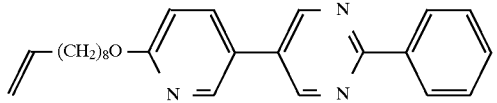

The synthesis was carried out analogously to Example 27 from 2-phenyl-5-bromopyrimidine and 2-decenyloxypyridine-5-boronic acid.

The compound has the following phase sequence:

X 87 $S_A$ 125 I

EXAMPLE 29

5-(2-Decyloxypyrimid-5-yl)-2-phenylpyridine

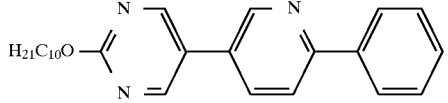

The synthesis was carried out analogously to Example 27 from 2-decenyloxy-5-bromopyrimidine and 2-phenylpyridine-5-boronic acid.

The compound has the following phase sequence:

X 125 $S_A$ 154 I

EXAMPLE 30

2-[2-(9-Decenyloxy)pyrid-5-yl]-5-phenylpyrimidine

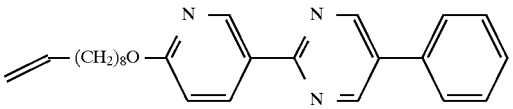

The synthesis was carried out analogously to Example 27 from 2-bromo-5-phenylpyrimidine and 2-decenylpyridine-5-boronic acid.

The compound has the following phase sequence:

X 96 $S_A$ 91 I

EXAMPLE 31

5-(5-Dodecylpyrimid-2-yl)-2-phenylpyridine

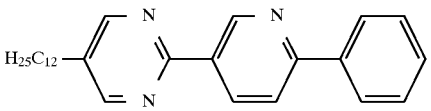

The synthesis was carried out analogously to Example 27 from 2-bromo-5-dodecylpyrimidine and 2-phenylpyridine-5-boronic acid.

The compound has the following phase sequence:

X 76 $S_A$ 130 I

Use Example 1

The mixture comprises the components

| | | |
|---|---|---|
| 1 | 5-octyloxy-2-(4-hexyloxyphenyl)-pyrimidine | 7.8 mol % |
| 2 | 5-octyloxy-2-(4-butoxyphenyl)-pyrimidine | 8.3 mol % |
| 3 | 5-octyloxy-2-(4-decyloxyphenyl)pyrimidine | 6.5 mol % |
| 4 | 5-octyloxy-2-(4-octyloxyphenyl)-pyrimidine | 3.6 mol % |
| 5 | 5-octyl-2-(4-hexyloxyphenyl)pyrimidine | 12.5 mol % |
| 6 | 5-octyl-2-(4-octyloxyphenyl)pyrimidine | 11.2 mol % |
| 7 | 5-octyl-2-(4-decyloxyphenyl)pyrimidine | 8.3 mol % |
| 8 | 4-(5-dodecylpyrimidin-2-yl)phenyl trans-4-pentylcyclohexanecarboxylate | 12.3 mol % |
| 9 | (2S,3S)-2-[4-(5-octylpyrimidin-2-yl)-phenyloxy]methyl-3-butyloxirane | 5.7 mol % |
| 10 | 4-(2-octyloxypyrimidin-5-yl)phenyl (2R,3R)-3-propyloxirane-2-carboxylate | 6.5 mol % |
| 11 | (S)-4-(2-octyloxypyrimidin-5-yl)phenyl-(spiro-(1,3-dioxolane-2,1-cyclohexan)-4-yl) methyl ether | 3.4 mol % |
| 12 | 2-(4-nonylphenyl)-5-phenyl-1,3,4-thiadiazole | 3.0 mol % |
| 13 | 2-(4-decylphenyl)-5-phenyl-1,3,4-thiadiazole | 3.0 mol % |
| 14 | 2-(4-octyloxyphenyl)-5-phenylpyrimidine | 3.9 mol % |
| 15 | 2-(4-decyloxyphenyl)-5-phenyl-1,3,4-thiadiazole | 2.5 mol % |
| 16 | 4,7,13,16,21,24-hexaoxa-1,10-diazabicyclo-(8.8.8)hexacosane (® Kryptofix 222) | 1.5 mol % |

The mixture has the following liquid-crystalline phase ranges:

X −9 $S^*_C$ 56 $S_A$ 70 N*82 I

The ready-to-use ferroelectric mixture was introduced into a polyimide-coated cell with a thickness of 2 μm and subjected to a rectangular field treatment of 15 V/μm at a frequency of 10 Hz for 10 minutes. The sample subsequently switched at an applied field strength of 10 V/μm at a pulse width of 91 μs.

A liquid-crystal mixture differing from the abovementioned only in that components 12–15 (compounds according to the invention) were not added has the phase ranges:

X −4 S*$_C$ 58 S$_A$ 67 N 82 I

The minimum pulse duration at which the sample switches at a field strength of 10 V/μm is 115 μs.

If 1.5 mol % of component 16 are replaced by 0.5 mol % of 1-(tert-butylcarbonyl)-1-aza-4,7,10,13-tetraoxacyclopentadecane(13-1,4,7,10), the sample switches at a field strength of 18 V/μm at a pulse width of 50 μs.

Use Example 2

The mixture comprises the components

| | | |
|---|---|---|
| 1 | 5-octyloxy-2-(4-hexyloxyphenyl)-pyrimidine | 8.6 mol % |
| 2 | 5-octyloxy-2-(4-butoxyphenyl)-pyrimidine | 9.1 mol % |
| 3 | 5-octyloxy-2-(4-decyloxyphenyl)-pyrimidine | 7.1 mol % |
| 4 | 5-octyloxy-2-(4-octyloxyphenyl)pyrimidine | 4.0 mol % |
| 5 | 5-octyl-2-(4-hexyloxyphenyl)pyrimidine | 13.7 mol % |
| 6 | 5-octyl-2-(4-octyloxyphenyl)pyrimidine | 12.3 mol % |
| 7 | 5-octyl-2-(4-decyloxyphenyl)pyrimidine | 9.1 mol % |
| 8 | 4-(5-dodecylpyrimidin-2-yl)phenyl trans-4-pentylcyclohexanecarboxylate | 13.5 mol % |
| 9 | (2S,3S)-2-[4-(5-octylpyrimidin-2-yl)-phenyloxy]methyl-3-butyloxirane | 6.3 mol % |
| 10 | 4-(2-octyloxypyrimidin-5-yl)phenyl (2R,3R)-3-propyloxirane-2-carboxylate | 7.1 mol % |
| 11 | (S)-4-(2-octyloxypyrimidin-5-yl)phenyl-(spiro-(1,3-dioxolane-2,1-cyclohexan)-4-yl) methyl ether | 3.7 mol % |
| 12 | 5-(5-dodecylpyrimid-1-yl)-2-phenyl-pyridine | 5.0 mol % |
| 13 | 1-(tert-butylcarbonyl)-1-aza-4,7,10,13-tetraoxacyclopentadecane-(13-1,4,7,10) | 0.5 mol % |

The mixture has the following liquid-crystalline phase ranges:

S*$_C$ 57 S$_A$ 71 N*81 I

The ready-to-use ferroelectric mixture was introduced into a polyimide-coated cell with a thickness of 2 μm and subjected to a rectangular field treatment of 15 V/μm at a frequency of 10 Hz for 10 minutes. The sample subsequently switched at an applied field strength of 15.2 V/μm at a pulse width of 50 μs.

Use Example 3

The mixture comprises the components

| | | |
|---|---|---|
| 1 | 5-octyloxy-2-(4-hexyloxyphenyl)-pyrimidine | 8.6 mol % |
| 2 | 5-octyloxy-2-(4-butoxyphenyl)-pyrimidine | 9.1 mol % |
| 3 | 5-octyloxy-2-(4-decyloxyphenyl)-pyrimidine | 7.1 mol % |
| 4 | 5-octyloxy-2-(4-octyloxyphenyl)-pyrimidine | 4.0 mol % |
| 5 | 5-octyl-2-(4-hexyloxyphenyl)pyrimidine | 13.7 mol % |
| 6 | 5-octyl-2-(4-octyloxyphenyl)pyrimidine | 12.3 mol % |
| 7 | 5-octyl-2-(4-decyloxyphenyl)pyrimidine | 9.1 mol % |
| 8 | 4-(5-dodecylpyrimidin-2-yl)phenyl trans-4-pentylcyclohexanecarboxylate | 13.5 mol % |
| 9 | (2S,3S)-2-[4-(5-octylpyrimidin-2-yl)-phenyloxy]methyl-3-butyloxirane | 6.3 mol % |
| 10 | 4-(2-octyloxypyrimidin-5-yl)phenyl (2R,3R)3-propyloxirane-2-carboxylate | 7.1 mol % |
| 11 | (S)-4-(2-octyloxypyrimidin-5-yl)phenyl-(spiro-(1,3-dioxolane-2,1-cyclohexan)-4-yl) methyl ether | 3.7 mol % |
| 12 | 2-(2-[9-decenyloxy]pyridin-5-yl)-2-phenyl-pyrimidine | 5.0 mol % |
| 13 | 1-(tert-butylcarbonyl)-1-aza-4,7,10,13-tetraoxacyclopentadecane-(13-1,4,7,10) | 0.5 mol % |

The mixture has the following liquid-crystalline phase ranges:

S*$_C$ 62 S$_A$ 76 N*83 I

The ready-to-use ferroelectric mixture was introduced into a polyimide-coated cell with a thickness of 2 μm and subjected to a rectangular field treatment of 15 V/μm at a frequency of 10 Hz for 10 minutes. The sample subsequently switched at an applied field strength of 12.7 V/μm at a pulse width of 50 μs.

Use Example 4

The mixture comprises the components

| | | |
|---|---|---|
| 1 | 5-octyloxy-2-(4-hexyloxyphenyl)-pyrimidine | 8.6 mol % |
| 2 | 5-octyloxy-2-(4-butoxyphenyl)-pyrimidine | 9.1 mol % |
| 3 | 5-octyloxy-2-(4-decyloxyphenyl)-pyrimidine | 7.1 mol % |
| 4 | 5-octyloxy-2-(4-octyloxyphenyl)-pyrimidine | 4.0 mol % |
| 5 | 5-octyl-2-(4-hexyloxyphenyl)pyrimidine | 13.7 mol % |
| 6 | 5-octyl-2-(4-octyloxyphenyl)pyrimidine | 12.3 mol % |
| 7 | 5-octyl-2-(4-decyloxyphenyl)pyrimidine | 9.1 mol % |
| 8 | 4-(5-dodecylpyrimidin-2-yl)phenyl trans-4-pentylcyclohexanecarboxylate | 13.5 mol % |
| 9 | (2S,3S)-2-[4-(5-octylpyrimidin-2-yl)-phenyloxy]methyl-3-butyloxirane | 6.3 mol % |
| 10 | 4-(2-octyloxypyrimidin-5-yl)phenyl (2R,3R)-3-propyloxirane-2-carboxylate | 7.1 mol % |
| 11 | (S)-4-(2-octyloxypyrimidin-5-yl)phenyl-(spiro-(1,3-dioxolane-2,1-cyclohexan)-4-yl) methyl ether | 3.7 mol % |
| 12 | 4-(pyrimidin-2-yl)phenyl 3-(4-ethylcyclo-hexyl) propanoate | 5.0 mol % |
| 13 | 1-(tert-butylcarbonyl)-1-aza-4,7,10,13-tetraoxacyclopentadecane-(13-1,4,7,10) | 0.5 mol % |

The mixture has the following liquid-crystalline phase ranges:

S*$_C$ 57 S$_A$ 63 N*79 I

The ready-to-use ferroelectric mixture was introduced into a polyimide-coated cell with a thickness of 2 μm and subjected to a rectangular field treatment of 15 V/μm at a frequency of 10 Hz for 10 minutes. The sample subsequently switched at an applied field strength of 17.4 V/μm at a pulse width of 50 μs.

Use Example 5

The mixture comprises the components

| | | |
|---|---|---|
| 1 | 5-octyloxy-2-(4-hexyloxyphenyl)-pyrimidine | 8.7 mol % |
| 2 | 5-octyloxy-2-(4-butoxyphenyl)-pyrimidine | 9.2 mol % |
| 3 | 5-octyloxy-2-(4-decyloxyphenyl)-pyrimidine | 7.2 mol % |
| 4 | 5-octyloxy-2-(4-octyloxyphenyl)-pyrimidine | 4.0 mol % |
| 5 | 5-octyl-2-(4-hexyloxyphenyl)pyrimidine | 13.9 mol % |
| 6 | 5-octyl-2-(4-octyloxyphenyl)pyrimidine | 12.4 mol % |
| 7 | 5-octyl-2-(4-decyloxyphenyl)pyrimidine | 9.2 mol % |
| 8 | 4-(5-dodecylpyrimidin-2-yl)phenyl | 13.6 mol % |

-continued

| | | |
|---|---|---|
| | trans-4-pentylcyclohexanecarboxylate | |
| 9 | (2S,3S)-2-[4-(5-octylpyrimidin-2-yl)-phenyloxy]methyl-3-butyloxirane | 6.3 mol % |
| 10 | 4-(2-octyloxypyrimidin-5-yl)phenyl (2R,3R)-3-propyloxirane-2-carboxylate | 7.2 mol % |
| 11 | (S)-4-(2-octyloxypyrimidin-5-yl)phenyl-(spiro-(1,3-dioxolane-2,1-cyclo-hexan)-4-yl) methyl ether | 3.8 mol % |
| 12 | 2-(pyridin-4-yl)-5-(4-decyloxyphenyl)-pyrimidine | 4.0 mol % |
| 13 | 1-(tert-butylcarbonyl)-1-aza-4,7,10,13-tetraoxacyclopentadecane-(13-1,4,7,10) | 0.5 mol % |

The mixture has the following liquid-crystalline phase ranges:

$S^*_C$ 55 $S_A$ 79 N* 84 I

The ready-to-use ferroelectric mixture was introduced into a polyimide-coated cell with a thickness of 2 µm and subjected to a rectangular field treatment of 15 V/µm at a frequency of 10 Hz for 10 minutes. The sample subsequently switched at an applied field strength of 10.4 V/µm at a pulse width of 50 µs.

Use Example 6

The mixture comprises the components

| | | |
|---|---|---|
| 1 | 5-octyloxy-2-(4-hexyloxyphenyl)-pyrimidine | 8.1 mol % |
| 2 | 5-octyloxy-2-(4-butoxyphenyl)-pyrimidine | 8.6 mol % |
| 3 | 5-octyloxy-2-(4-decyloxyphenyl)-pyrimidine | 6.8 mol % |
| 4 | 5-octyloxy-2-(4-octyloxyphenyl)-pyrimidine | 3.7 mol % |
| 5 | 5-octyl-2-(4-hexyloxyphenyl)pyrimidine | 13.0 mol % |
| 6 | 5-octyl-2-(4-octyloxyphenyl)pyrimidine | 11.6 mol % |
| 7 | 5-octyl-2-(4-decyloxyphenyl)pyrimidine | 8.6 mol % |
| 8 | 4-(5-dodecylpyrimidin-2-yl)phenyl trans-4-pentylcyclohexanecarboxylate | 12.8 mol % |
| 9 | (2S,3S)-2-[4-(5-octylpyrimidin-2-yl)-phenyloxy]methyl-3-butyloxirane | 5.9 mol % |
| 10 | 4-(2-octyloxypyrimidin-5-yl)phenyl (2R,3R)-3-propyloxirane-2-carboxylate | 6.7 mol % |
| 11 | (S)-4-(2-octyloxypyrimidin-5-yl)phenyl-(spiro(1,3-dioxolane-2,1-cyclo-hexan)-4-yl) methyl ether | 3.5 mol % |
| 12 | 2-(4-nonylphenyl)-5-phenyl-1,3,4-oxa-diazole | 10.0 mol % |
| 13 | 1-(tert-butylcarbonyl)-1-aza-4,7,10,13-tetraoxacyclopentadecane-(13-1,4,7,10) | 0.5 mol % |

The mixture has the following liquid-crystalline phase ranges:

$S^*_C$ 58 $S_A$ 65 N 77 I

The ready-to-use ferroelectric mixture was introduced into a polyimide-coated cell with a thickness of 2 µm and subjected to a rectangular field treatment of 15 V/µm at a frequency of 10 Hz for 10 minutes. The sample subsequently switched at an applied field strength of 14.5 V/µm at a pulse width of 50 µs.

Comparison of the switching fields for mixtures of the use examples 2 to 6 with the switching field of the comparison mixture mentioned in use example 1 confirms that the use of the compounds according to the invention allows a considerable reduction to be achieved in the field strength required.

Use Example 7

A ferroelectric mixture comprises the components

| | |
|---|---|
| 2-(4-decyloxyphenyl)-5-phenyl-1,3,4-thiadiazole | 10.0 mol % |
| 5-octyl-2-(4-hexyloxyphenyl)pyrimidine | 11.2 mol % |
| 5-octyl-2-(4-decyloxyphenyl)pyrimidine | 7.5 mol % |
| 5-decyl-2-(4-hexyloxyphenyl)pyrimidine | 7.2 mol % |
| 5-octyl-2-(4-(7-cyclopropylheptyloxy)phenyl)-pyridine | 6.0 mol % |
| 5-octyl-2-(4-(6-cyclopropyl)hexylcarbonyloxy-phenyl) pyrimidine | 7.5 mol % |
| 5-(8-cyclopropyloctyloxy)-2-(4-transpentyl-cyclohexyl-4-phenyl)pyrimidine | 8.7 mol % |
| 4-(8-cyclopropyloctyl)pyrimidin-2-ylphenyl trans-4-pentylcyclohexanecarboxylate | 5.3 mol % |
| 5-(5-cyclopropylpentyloxy)-2-(4-hexyloxy-phenyl) pyrimidine | 8.0 mol % |
| (2S,3S)-2-(4-(5-(9-deconyloxypyrimidin-2-yl)-phenyloxy)methyl-3-butyloxirane | 11.5 mol % |
| (2S,3S)-2-(4-(5-(7-octenyloxypyrimidin-2-yl)-phenyloxy)methyl-3-butyloxirane | 3.4 mol % |
| (2S,3S)-2-(4-(5-(5-hexenyloxypyrimidin-2-yl)-phenyloxy)methyl-3-butyloxirane | 3.4 mol % |
| (S)-4-(5-octyloxypyrimidin-2-yl)phenyl-2,2-dimethyl-1,3-dioxlian)-4-yl) methyl ether | 1.7 mol % |
| 4-(2-undecyloxypyrimidin-5-yl) phenyl (2R,3R)-3-propyloxirane-2-carboxylate | 6.6 mol % |
| crown ether (18-crown-6) | 2.0 mol % |

The mixture has the following liquid-crystalline phase ranges:

$S^*_C$ 60 $S_A$ 74 N* 83 I and has a spontaneous polarization of 41 nC/cm² at 25° C. In a 2 µm cell at 25° C., the mixture switches with a response time of 58 µs in an electric field of 10 V/µm.

Use Example 8

A ferroelectric mixture comprises the components

| | |
|---|---|
| 2-(4-decylphenyl)-5-phenyl-1,3,4-thiadiazole | 10.0 mol % |
| 5-octyl-2-(4-hexyloxyphenyl)pyrimidine | 11.2 mol % |
| 5-octyl-2-(4-decyloxyphenyl)pyrimidine | 7.5 mol % |
| 5-decyl-2-(4-hexyloxyphenyl)pyrimidine | 7.2 mol % |
| 5-octyl-2-(4-(7-cyclopropylheptyloxy)phenyl)-pyridine | 6.0 mol % |
| 5-octyl-2-(4-(6-cyclopropyl)hexylcarbonyloxy-phenyl)pyrimidine | 7.5 mol % |
| 5-(8-cyclopropyloctyloxy)-2-(4-transpentyl-cyclohexyl-4-phenyl)pyrimidine | 8.7 mol % |
| 4-(8-cyclopropyloctyl)pyrimidin-2-ylphenyl trans-4-pentylcyclohexanecarboxylate | 5.3 mol % |
| 5-(5-cyclopropylpentyloxy)-2-(4-hexyloxy-phenyl)pyrimidine | 8.0 mol % |
| (2S,3S)-2-(4-(5-(8-decenyloxypyrimidin-2-yl)-phenyloxy)methyl-3-butyloxirane | 11.5 mol % |
| (2S,3S)-2-(4-(5-(7-octenyloxypyrimidin-2-yl)-phenyloxy)methyl-3-butyloxirane | 3.4 mol % |
| (2S,3S)-2-(4-(5-(5-hexenyloxypyrimidin-2-yl)-phenyloxy)methyl-3-butyloxirane | 3.4 mol % |
| (S)-4-(5-octyloxypyrimidin-2-yl)phenyl-2,2-dimethyl-1,3-dioxolan)-4-yl)methyl ether | 1.7 mol % |
| 4-(2-undecyloxypyrimidin-5-yl)phenyl (2R,3R)-3-propyloxirane-2-carboxylate | 6.6 mol % |
| crown ether (18-crown-6) | 2.0 mol % |

The mixture has the following liquid-crystalline phase ranges:

$S^*_C$ 56 $S_A$ 68 N* 80 I and has a spontaneous polarization of 38 nC/cm² at 25° C. In a 2 µm cell at 25° C., the mixture switches with a response time of 63 µS in an electric field of 10 V/µm.

A liquid-crystal mixture which differs from the two last-mentioned mixtures only in that the first (novel) component has not been added has the phase ranges:

$S^*_C$ 58 $S_A$ 67 N*78 I

The polarization is 46 nC/cm², and the response time is 73 µs at a field strength of 10 V/µm⁻¹.

These examples confirm that ferroelectric mixtures which have short response times can be prepared using the components according to the invention.

We claim:

1. A method for producing ferroelectric liquid-crystal mixtures, which comprises adding 0.01 to 60% by weight of one or more compounds of the formula (I)

$$R^1\!-\!(A^1)_a(\!-\!M^1)_b\!-\!(\!-\!A^2)_c(\!-\!M^2)_d(\!-\!A^3)_e(\!-\!M^3)_f(\!-\!A^4)_g\!-\!H \quad (I)$$

in which the symbols and indices have the following meanings:

$R^1$ is a straight-chain or branched alkyl radical having 1 to 22 carbon atoms (with or without an asymmetrical carbon atom) in which, in addition, it is possible for one or two non-adjacent —CH₂— groups to be replaced by —O—, —S—, —CO—, —CO—O—, —O—CO—, —CO—S—, —S—CO—, —O—CO—O—, —CH=CH—, —C≡C—, Δ or —Si(CH₃)₂—, and in which, in addition, one or more hydrogen atoms of the alkyl radical may be substituted by F, Cl, Br or CN, or is one of the chiral groups below:

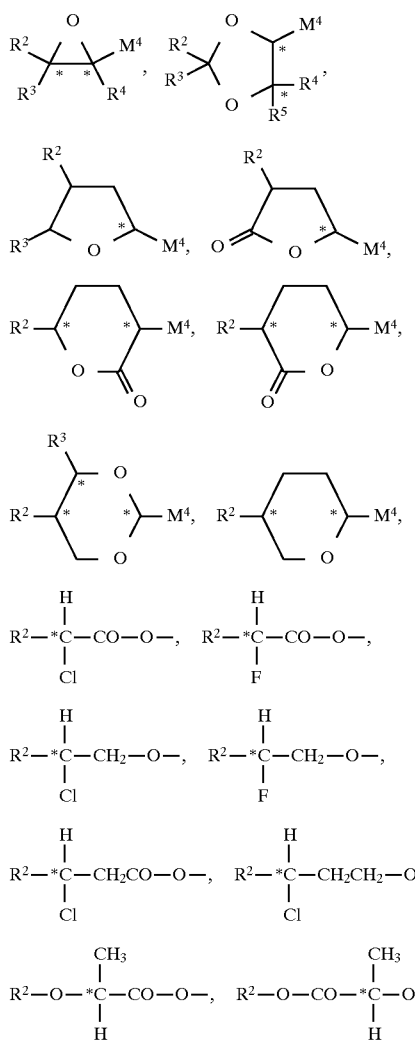

$R^2$, $R^3$, $R^4$ and $R^5$, independently of one another, are H or a straight-chain or branched alkyl radical having 1 to 22 carbon atoms in which, in addition, it is possible for one or two non-adjacent —CH₂— groups to be replaced by —O—, —S—, —CO—, —CO—O—, —O—CO—, —CO—S—, —S—CO—, —O—CO—O—, —CH=CH—, —C≡C—, Δ or —Si(CH₃)₂—, or $R^2$ and $R^3$ together may alternatively be —(CH₂)₄— or —(CH₂)₅— if they are bonded as substituents to a dioxolane system;

$A^1$, $A^2$, $A^3$ and $A^4$ are identical or different and are 1,4-phenylene, in which one or two hydrogen atoms may be replaced by F, Cl and/or CN, pyrazine-2,5-diyl, pyridazine-3,6-diyl, pyridine-2,5-diyl, pyrimidine-2,5-diyl, in which one or two hydrogen atoms may be replaced by F, trans-1,4-cyclohexylene, in which one or two hydrogen atoms may be replaced by —CN and/or —CH₃, 1,3,4-thiadiazole-2,5-diyl, 1,3-dioxane-2,5-diyl, 1,3-dithiane-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2,5-diyl, naphthalene-2,6-diyl, bicyclo[2.2.2]octane-1,4-diyl, 1,3-dioxaborinane-2,5-diyl or trans-decalin-2,6-diyl;

$M^1$, $M^2$ and $M^3$ are identical or different and are —O—, —S—, —CO—, —CO—O—, —O—CO—, —CO—S—, —S—CO—, —O—CO—O—, —CH₂—O—, —O—CH₂—, —CH₂CH₂—, —CH=CH—, or —C≡C—;

$M^4$ is —CH₂—O—, —O—CH₂—, —CO—O—, —O—CO— or a single bond;

a, b, c, d, e and f are zero or one, with the proviso that the sum a+c+e+g is 1, 2, 3 or 4, g is one and

* is a chiral center;

to one or more compounds having nematic, cholesteric and/or smectic phases.

2. A ferroelectric liquid-crystal mixture comprising one or more compounds of the formula (I)

$$R^1\!-\!(A^1)_a(\!-\!M^1)_b\!-\!(\!-\!A^2)_c(\!-\!M^2)_d(\!-\!A^3)_e(\!-\!M^3)_f(\!-\!A^4)_g\!-\!H \quad (I)$$

in which the symbols and indices have the following meanings:

$R^1$ is a straight-chain or branched alkyl radical having 1 to 22 carbon atoms (with or without an asymmetrical carbon atom) in which, in addition, it is possible for one or two non-adjacent —CH₂— groups to be replaced by —O—, —S—, —CO—, —CO—O—, —O—CO—, —CO—S—, —S—CO—, —O—CO—O—, —CH=CH—, —C≡C—, Δ or —Si(CH₃)₂—, and in which, in addition, one or more hydrogen atoms of the alkyl radical may be substituted by F, Cl, Br or CN, or is one of the chiral groups below:

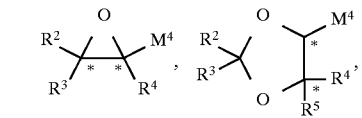

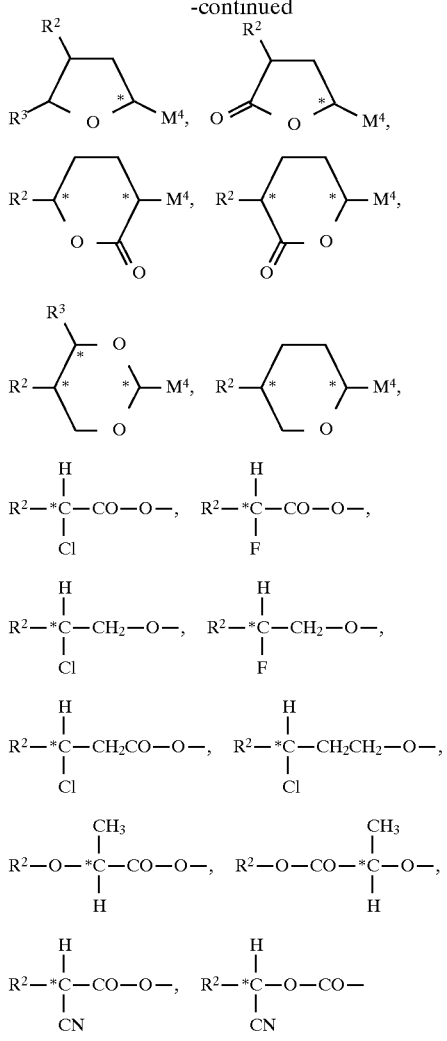

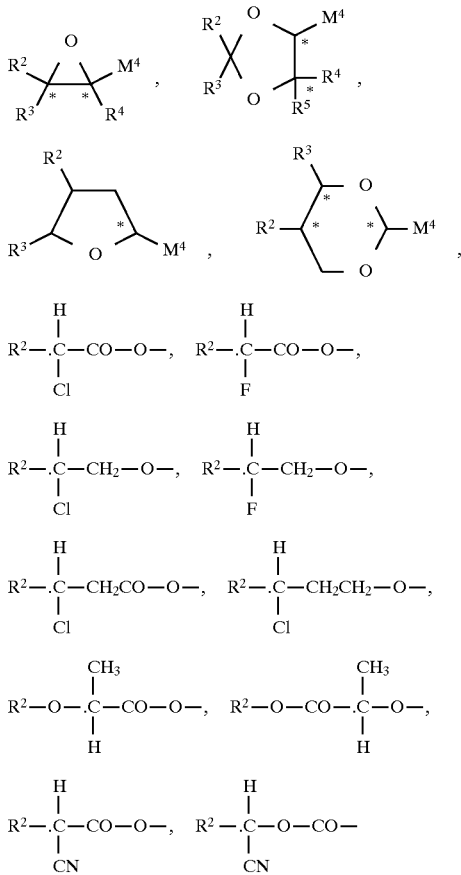

R², R³, R⁴ and R⁵, independently of one another, are H or a straight-chain or branched alkyl radical having 1 to 22 carbon atoms in which, in addition, it is possible for one or two non-adjacent —CH₂— groups to be replaced by —O—, —S—, —CO—, —CO—O—, —O—CO—, —CO—S—, —S—CO—, —O—CO—O—, —CH=CH—, —C≡C—, Δ or —Si(CH₃)₂—, or R² and R³ together may alternatively be —(CH₂)₄— or —(CH₂)₅— if they are bonded as substituents to a dioxolane system;

A¹, A², A³ and A⁴ are identical or different and are 1,4-phenylene, in which one or two hydrogen atoms may be replaced by F, Cl and/or CN, pyrazine-2,5-diyl, pyridazine-3,6-diyl, pyridine-2,5-diyl, pyrimidine-2,5-diyl, in which one or two hydrogen atoms may be replaced by F, trans-1,4-cyclohexylene, in which one or two hydrogen atoms may be replaced by —CN and/or —CH₃, 1,3,4-thiadiazole-2,5-diyl, 1,3-dioxane-2,5-diyl, 1,3-dithiane-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2,5-diyl, naphthalene-2,6-diyl, bicyclo[2.2.2]octane-1,4-diyl, 1,3-dioxaborinane-2,5-diyl or trans-decalin-2,6-diyl;

M¹, M² and M³ are identical or different and are —O—, —S—, —CO—, —CO—O—, —O—CO—, —CO—S—, —S—CO—, —O—CO—O—, —CH₂—O—, —O—CH₂—, —CH₂CH₂—, —CH=CH—, or —C≡C—;

M⁴ is —CH₂—O—, —O—CH₂—, —CO—O—, —O—CO—, or a single bond;

a, b, c, d, e and f are zero or one, with the proviso that the sum a+c+e+g is 1, 2, 3 or 4, g is one and

* is a chiral center.

3. A ferroelectric liquid-crystal mixture as claimed in claim 2, wherein the liquid-crystal mixture is ferroelectric.

4. A ferroelectric liquid-crystal mixture as claimed in claim 2, comprising from 0.01 to 60% of one or more compounds of the general formula (I).

5. A mixture as claimed in claim 2, in which the symbols and indices have the following meanings:

R¹ is a straight-chain or branched alkyl radical having 1 to 22 carbon atoms (with or without an asymmetrical carbon atom) in which, in addition, one or two non-adjacent —CH₂— groups may be replaced by —O—, —S—, —CO—, —CO—O—, —O—CO—, —O—CO—O—, —CH=CH—, —C≡C—, Δ or —Si(CH₃)₂—, or is one of the chiral groups below:

R², R³, R⁴ and R⁵, independently of one another, are H or a straight-chain or branched alkyl radical having 1 to 22 carbon atoms in which, in addition, one or two non-adjacent —CH₂— groups may be replaced by —O—, —S—, —CO—, —CO—O—, —O—CO—, —CO—S—, —S—CO—, —O—CO—O—, —CH=CH—, —C≡C—, Δ or —Si(CH₃)₂—, or R² and R³ together may alternatively be —(CH₂)₄— or —(CH₂)₅— if they are bonded as substituents to a dioxolane system;

A¹, A², A³ and A⁴ are identical or different and are 1,4-phenylene, pyrazine-2,5-diyl, pyridazine-3,6-diyl, pyridine-2,5-diyl, pyrimidine-2,5-diyl, trans-1,4- cyclohexylene, 1,3,4-thidiazole-2,5-diyl, 1,3-dioxane-2,5-diyl, naphthalene-2,6-diyl or bicyclo[2.2.2]octane-1,4-diyl;

$M^1$, $M^2$ and $M^3$ are identical or different and are —O—, —CO—, —CO—O—, —O—CO—, —CH$_2$—O—, —O—CH$_2$—, —CH$_2$CH$_2$—, —CH=CH— or —C≡C—;

$M^4$ is —CH$_2$—O—, —O—CH$_2$—, —CO—O—, —O—CO—, or a single bond.

6. A mixture as claimed in claim 2, in which the symbols and indices have the following meanings:

$R^1$ is a straight-chain or branched alkyl radical having 1 to 22 carbon atoms (with or without an asymmetrical carbon atom) in which, in addition, one or two non-adjacent —CH$_2$— groups may be replaced by —O—, —CO—, —CO—O—, —O—CO—, —CH=CH—, —C≡C—, Δ or —Si(CH$_3$)$_2$—, or is one of the chiral groups below:

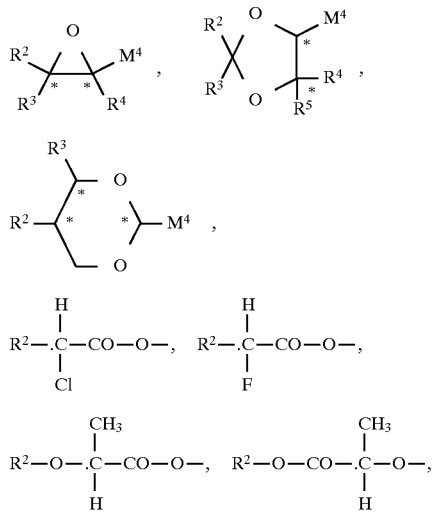

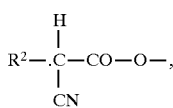

$R^2$, $R^3$, $R^4$ and $R^5$, independently of one another, are H or a straight-chain or branched alkyl radical having 1 to 22 carbon atoms in which, in addition, one or two non-adjacent —CH$_2$— groups may be replaced by —O—, —S—, —CO—, —CO—O—, —O—CO—, —CO—S—, —S—CO—, —O—CO—O—, —CH=CH—, —C≡C—, Δ or —Si(CH$_3$)$_2$—, or $R^2$ and $R^3$ together may alternatively be —(CH$_2$)$_4$— or —(CH$_2$)$_5$— if they are bonded as substituents to a dioxolane system;

$A^1$, $A^2$, $A^3$ and $A^4$ are identical or different and are 1,4-phenylene, pyrazine-2,5-diyl, pyridine-2,5-diyl, pyrimidine-2,5-diyl, trans-1,4-cyclohexylene, 1,3,4-thiadiazole-2,5-diyl, naphthalene-2,6-diyl or 1,3-dioxane-2,5-diyl;

$M^1$, $M^2$ and $M^3$ are identical or different and are —O—, —CO—O—, —O—CO—, —CH$_2$—O—, —O—CH$_2$—, —CH$_2$—CH$_2$—, —CH=CH— or —C≡C—;

$M^4$ is —CH$_2$—O—, —O—CH$_2$—, —CO—O—, —O—CO— or a single bond.

7. A mixture as claimed in claim 2, wherein $R^1$ is an alkyl radical having 1 to 22 carbon atoms, in which one —CH$_2$— group may be replaced by —O—, Δ, —CH=CH— or —Si(CH$_3$)$_2$—, or is the chiral group

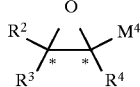

and the $(—A^1)_a(—M^1)_b(—A^2)_c(—M^2)_d(—A^3)_e(—M^3)_f(—A^4)_g$ group has the following meaning:

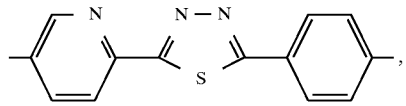

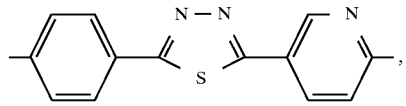

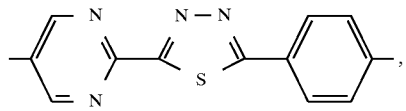

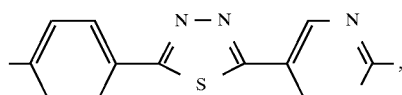

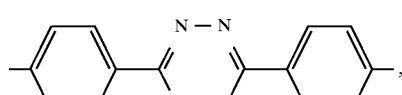

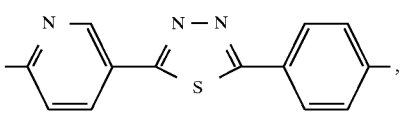

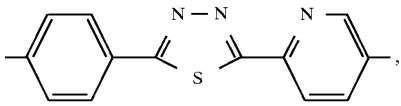

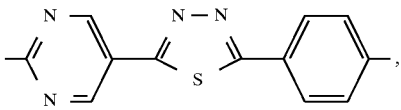

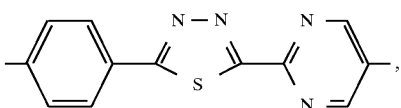

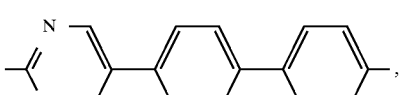

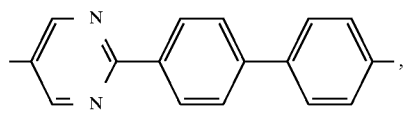
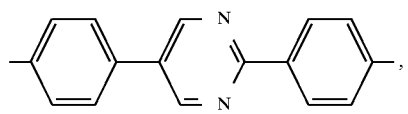
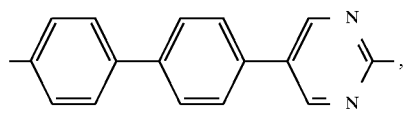
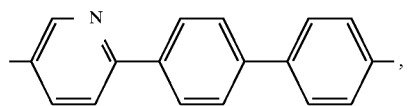
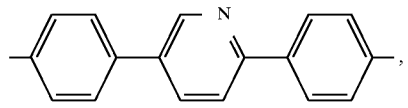
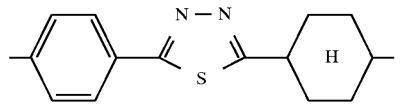
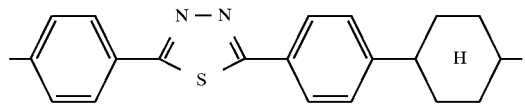
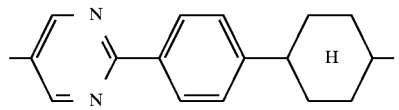
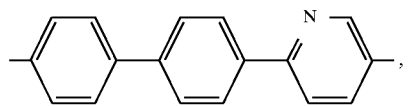
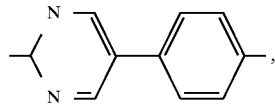
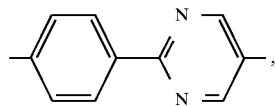
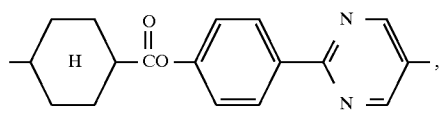
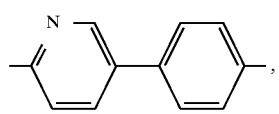
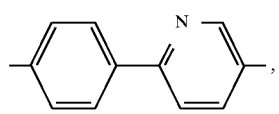
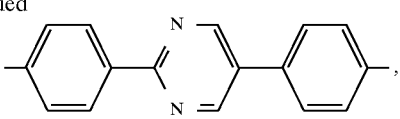
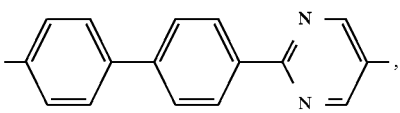
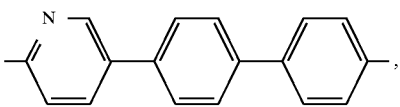
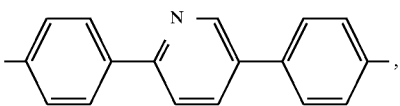
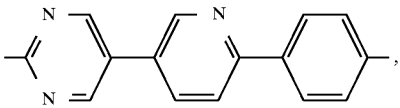
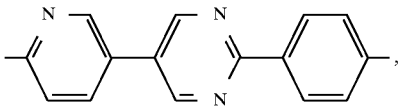
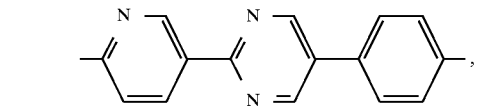
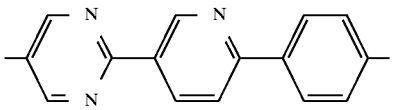
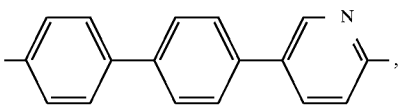
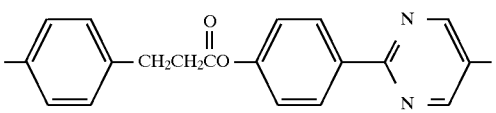

-continued
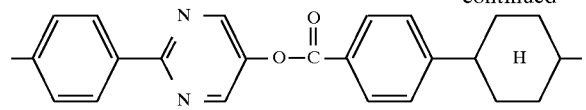
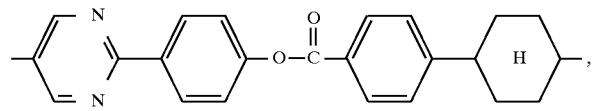
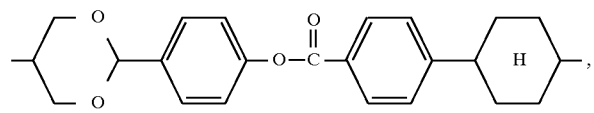
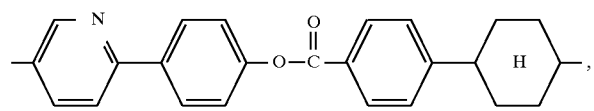
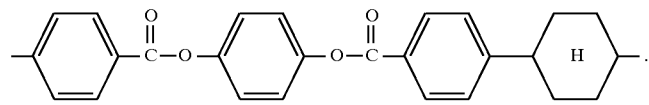
* * * * *